United States Patent [19]

Shibata et al.

[11] Patent Number: 5,395,641
[45] Date of Patent: Mar. 7, 1995

[54] PROCESS FOR DETECTING VOIDS IN CERAMIC BODIES

[75] Inventors: Kazuyoshi Shibata; Toshihiko Suzuki, both of Nagoya, Japan

[73] Assignee: NGK Insulators, Ltd., Japan

[21] Appl. No.: 852,644

[22] Filed: Mar. 17, 1992

[30] Foreign Application Priority Data

Mar. 20, 1991 [JP] Japan .................. 3-080631
Feb. 21, 1992 [JP] Japan .................. 4-035031

[51] Int. Cl.⁶ .................................. B05D 1/00
[52] U.S. Cl. .......................... 427/8; 427/10; 427/228; 427/245; 427/294
[58] Field of Search .......... 427/8, 245, 228, 10, 427/294

[56] References Cited

U.S. PATENT DOCUMENTS

| | | | |
|---|---|---|---|
| 4,034,286 | 7/1977 | Lev et al. | 324/71 |
| 4,443,278 | 4/1984 | Zingher | 29/830 |
| 4,578,279 | 3/1986 | Zingher | 427/10 |
| 4,894,251 | 1/1990 | Sieverin | 427/8 |

FOREIGN PATENT DOCUMENTS 739188 9/1943 Germany .
1263226 2/1972 United Kingdom .

OTHER PUBLICATIONS

De-Zeitschrift: Mitt. des Vereins Dt. Emailfachleute e.V. Patent Abstracts of Japan, vol. 14, No. 349, P-1084, Jul. 27, 1990; JP-2-126147.

*Primary Examiner*—Shrive Beck
*Assistant Examiner*—Vi Duong Dang
*Attorney, Agent, or Firm*—Parkhurst, Wendel & Rossi

[57] ABSTRACT

A process for detecting any defect in a ceramic body, including the steps of forming an electrically conductive layer in any such defects including fine voids present in the ceramic body, and then detecting presence or absence of the defect by measuring electrical conductivity between two given points shorted by the electrically conductive layer. The electrically conductive layer may be formed by penetrating an electrically conductive liquid into the defect. Alternatively, the electrically conductive layer may be formed by penetrating a penetrable liquid capable of forming the electrically conductive layer by thermal treatment or chemical treatment and thermally or chemically treating same.

11 Claims, 1 Drawing Sheet

PROCESS FOR DETECTING VOIDS IN CERAMIC BODIES

BACKGROUND OF THE INVENTION

(1) Field of the Invention

The present invention relates to a process for detecting defects including poor lamination and fine voids such as cracks present in ceramic bodies, such as laminates of ceramic planar sheets or members and ceramic structural bodies produced by pressing powders.

(2) Related Art Statement

Heretofore, the following techniques have been known as processes for detecting defects in ceramic bodies. For example, after a penetrable liquid containing a coloring matter penetrates fine voids present in a ceramic body, excess liquid attached to the surface of the ceramic body is washed off. As a result, no coloring matter remains attached onto a portion of the ceramic body free from defects, whereas the coloring matter remains on any portions containing defects. Therefore, defects can be detected by visual inspection. Further, a fluorescent paint may be used instead of the coloring matter. In this case, the fluorescent paint is impregnated into a ceramic body, and excess paint is washed off with water. Then, ultraviolet rays are irradiated upon the ceramic body in a dark chamber, so that any defects in the ceramic body can be detected from emission of light from the fluorescent paint impregnated into the defect. In the above techniques, presence or absence of the defect have been judged visually.

However, since the above-mentioned defect-detecting techniques are based on visual inspection, detecting ability depends upon the skill of inspecting individuals, whereby a small defect may be overlooked. Further, visual inspection hinders automation of consecutive steps, resulting in production processes having low productivity.

SUMMARY OF THE INVENTION

It is an object of the present invention to solve the above-mentioned problems, and to provide a process for detecting defects in ceramic bodies which can easily detect even extremely fine defects in the ceramic bodies irrespective of the skill of inspecting persons.

The process for detecting the defects in the ceramic body according to the present invention is characterized in that a highly electrically conductive liquid having excellent penetrability is penetrated into any defect present, including fine voids to form an electrically conductive layer in the defect. Alternatively, after a highly penetrable liquid capable of forming an electrically conductive layer by thermal treatment or chemical treatment is penetrated into such a defect, an electrically conductive layer is formed inside the defect by thermal or chemical treatment presence or absence of the defect is detected by measuring electric conductivity between two given points shorted by the electrically conductive layer.

The two points shortened may consist of one side surface and the other side surface of a partition wall of the ceramic body, or may be two points on the same surface of the ceramic body. An electrode preliminarily provided inside the ceramic body may be utilized as one of the two points to be shorted. Alternatively, as the above two points to be shorted, electrodes preliminarily provided on opposite surfaces of a partition wall of the ceramic body or electrodes provided on the same surface of the ceramic body may be utilized.

In the above construction, the electrically conductive liquid is introduced into or the electrically conductive layer is formed inside any defect involving a fine void present inside the ceramic body to make the defect portion electrically conductive. Thus, when electrical conductivity between the two points shorted by the electrically conductive liquid or the electrical conductive layer is measured, a large current flows through conductive material if such a defect exists. Therefore, the presence of the defect can be detected by comparing the intensity of this current with a specific current level. Accordingly, the presence or absence of the defect can be judged without relying on manual labor, so that the presence or absence of the defect can be automatically judged.

These and other objects, features and advantages of the invention will be appreciated upon reading of the following description of the invention when taken in conjunction with the attached drawing, with the understanding that some modifications, variations and changes of the same could be made by the skilled person in the art to which the invention pertains, without departing from the spirit of the invention or the scope of claims appended hereto.

BRIEF DESCRIPTION OF THE DRAWINGS

For a better understanding of the invention, reference is made to the attached drawing, wherein.

DETAILED DESCRIPTION OF THE INVENTION

Figure 1:
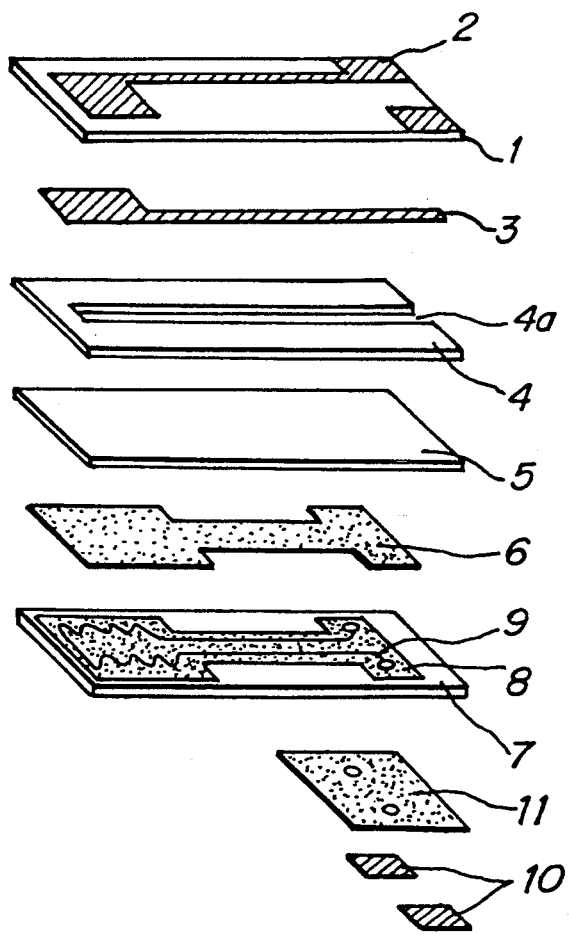
FIG. 1 is an exploded view of illustrating the structure of an example of an oxygen sensor to which the process for detecting the defect of the ceramic body according to the present invention is applicable.

The process for detecting the defect of the ceramic body according to the present invention is characterized in that (1) an electrically conductive material is first fed in any defect in the ceramic body to form an electrically conductive layer, (2) then electrical conductivity is measured between two points shorted through the electrically conductive layer, and (3) presence or absence of the defect is finally judged based on a comparison result between the detected electrical conductivity and a specific reference value.

In the process for detecting the defect of the ceramic body according to the present invention, the electrically conductive liquid or material is fed into the defect in the ceramic body. As materials of the ceramic bodies to which the present invention is applicable, almost all materials including electric materials, electron materials, magnetic materials, structural materials and cutting materials, such as zirconia, alumina, magnesia, mullite, ZnO, barium titanate, glass, $\beta$-alumina, silicon nitride, silicon carbide and boron nitride, may be recited. As the electrically conductive liquid used in the present invention, aqueous solutions of inorganic acids, organic compounds such as hydrochloric acid, nitric acid, acetic acid, formic acid and chloroacetic acid, their salts and bases such as ammonia and amines, may be used.

As the liquid which can form an electrically conductive layer by thermal treatment or chemical treatment, an aqueous solution of organic metal complexes and organic metal compounds, and electrolessly plating liquids may be used. Further, as the penetrable liquid which can be carbonized by thermal treatment to form an electrically conductive layer, for example, hydrocarbons such as alkylbenzene, liquids organic compounds containing hydrocarbons such as high boiling point alcohols or esters as main ingredients, and liquid containing organic dyes may be used. These organic compounds are, for example, p-isopropyl toluene, turpentine oil, n-decyl alcohol and phenylmethyl acetone.

The above electrically conductive liquid or the liquid capable of forming the electrically conductive layer by the thermal or chemical treatment is penetrated into a defect of the ceramic body. When this defect is small or when a liquid having low penetrability is used, the liquid may be assuredly penetrated into the defect by reducing pressure after the ceramic body is immersed into the liquid.

Next, electrical conductivity between any two points shortened by the electrically conductive layer is measured. Electrodes may be formed to examine the electrical conductivity between such two points as follows:

For example, when the electrically conductive liquid is used, electrodes may be positioned near the ceramic body. When the electrically conductive layer is formed by the thermal treatment or chemical treatment, the electrically conductive layer itself may be used as an electrode. Alternatively, a metal foil is press adhered onto the surface of the ceramic body. Further, the electrodes may be preliminarily provided, such as by screen printing, plating, vapor deposition or brushing. Such an electrode may be left if it is necessary for a final product, or if it is unnecessary, the electrode may be removed by a chemical or physical treatment after inspection is terminated.

Finally, the detected electrical conductivity is compared with a preliminarily determined value. Based on a comparison result, if the detected electrical conductivity is greater than the above preliminarily determined value, it is judged that the defect is present. On the other hand, if the detected electrical conductivity is nearly the same value as that preliminarily determined, it is judged that no defect is present. By so doing, the presence or absence of the defect can be detected. It is necessary that the above preliminarily determined value is preliminarily determined by actually examining the electrical conductivity of the ceramic body when voltage is applied thereto. The preliminarily determined value is obtained as follows. That is, to a ceramic body having no defect is applied voltage not to break the ceramic body, and intensity of current passing through the ceramic body is measured. An electroconductivity is determined from the thus measured current intensity, and is used as the "preliminarily determined value". The intensity of current passing through the ceramic body depends upon the material and size of the ceramic body, etc. Next, examples of actually detecting defects of ceramic bodies will be explained.

FIG. 1 is an exploded view of illustrating the structure of an example of oxygen sensors to which the process for detecting the defects of the ceramic bodies according to the present invention may be applied. In the oxygen sensor shown in FIG. 1, a solid electrolyte is denoted by reference numeral 1, and a measuring electrode 2 and a reference electrode 3 are provided on opposite surfaces of the solid electrolyte 1, respectively. Reference numeral 4 is a solid electrolyte having an air opening 4a. Reference numerals 5, 6, 7 and 8 are a solid electrolyte, a heater-protecting alumina layer, a solid electrolyte, and a heat-protecting alumina layer provided on the solid electrolyte, respectively. Reference numerals 9, 10 and 11 are a heater provided between the alumina layers 6 and 8, a heater terminal, and a layer for insulating the heater terminal, respectively. In the oxygen sensor having such a construction, the alumina layers 6 and 8 arranged to insulate the heater are made porous to mitigate stress produced due to difference in coefficient of thermal expansion between the alumina layers and the solid electrolyte such as zirconia.

Figure 2:
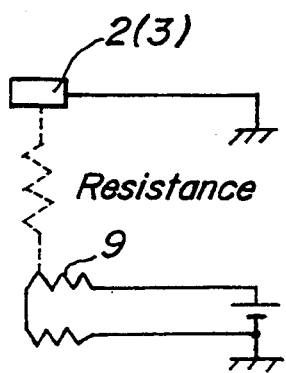
FIG. 2 is a view for illustrating a principle by which the defect is detected according to the process of the present invention.

In the illustrated embodiment, the heater 9 is buried in the porous alumina layers 6 and 8. The alumina layers themselves are completely isolated from the exterior with the solid electrolytes 5 and 7 made of dense zirconia. Therefore, even if the entire element is immersed into the liquid, the liquid will not penetrate to the alumina layer 6 or 8 unless a defect exists in the solid electrolyte 5 or 7. However, if a defect exists in the solid electrolyte 5 or 7 and extends up to the alumina layer 6 or 8, the liquid penetrates the porous layer 6 or 8. In this case, the penetrated liquid is converted to the electrically conductive layer by applying voltage to the heater 9. Then, when the temperature of the element increases upon application of voltage to the heater 9, the solid electrolyte comes to have electrical conductivity. Accordingly, leakage current flows between the electrode 2 or 3 and the heater 9 along a circuit shown in FIG. 2. By detecting intensity of this current, presence of a crack in a portion of the ceramic body surrounding the heater 9 can be judged. The above-mentioned measurement will be outlined based on the following specific example. If this measured current intensity exceeds a given value, for example, a worker is alarmed with a buzzer, so that the worker rejects the element. In this test, fine cracks which would not be discovered by a visual inspection could be detected. The above-mentioned measurement will be outlined based on the following specific example.

After an organic solvent containing an azo dye was placed in a beaker, an oxygen sensor as shown in FIG. 1 was completely immersed into the liquid. Then, after the beaker was placed in a sealed vessel and kept at a vacuum degree of a gauge pressure not less than 700 mmHg for 3 minutes, the vessel was opened to atmospheric pressure. The element was taken out from the beaker, and the organic solvent attached to the surface of the element was washed off with water. Then, after the element was dried at a temperature of 120° C. for not less than 1 hour, the organic solvent was carbonized. Since the carbonizing temperature depends upon the liquid used, the temperature cannot be definitely determined one-to-one. However, the carbonizing temperature may be appropriately about 300°-600° C. The keeping time may be about 1-5 minutes. In this embodiment, current was passed through the heater provided in the element, and the temperature on the surface of the element was kept at 400°-500° C. By so heating, the organic solvent was carbonized to exhibit electrical conductivity. When the leakage current was to be measured, the temperature of the element was held to be lower than the carbonizing temperature by about 100°-200° C, and intensity of current flowing the heater 9 and the measuring electrode 2 or the reference electrode 3 was measured. If such a measured current intensity exceeds a preliminarily determined value, for example, a worker may be alarmed by a buzzer, so that the worker may reject the element. In this test, a fine crack which would not be discovered by a visual inspection could be detected.

In the above test, explanation has been made with respect to the element equipped with the heater. If the element is provided with no heater, the ceramic body is placed in the electric furnace, and is heated in air at the above temperature to carbonize the organic solvent. Further, in the above test, explanation has been made with respect to the organic dye-containing organic solvent used as the penetrable liquid. Similar effects can be obtained by using a liquid having an electrical conductivity or a liquid capable of exhibiting the electrical conductivity by chemical treatment after the impregnation.

As is clear from the above-mentioned explanation, according to the present invention, the electrically conductive liquid having excellent penetrability is penetrated into any defect including fine voids in the ceramic body or a penetrable liquid capable of forming an electrically conductive layer by thermal treatment or chemical treatment is penetrated into the defect and an electrically conductive layer is formed in the defect by thermal treatment or the chemical treatment, and then the electrical conductivity between any two points shorted by the electrically conductive layer is measured. By so doing, presence or absence of defects inside the ceramic body can be detected. Therefore, even a fine defect can be accurately detected without relying upon visual inspection.

What is claimed is:

1. A process for detecting voids in a ceramic body, comprising:
   penetrating a penetrable liquid into any void present in the ceramic body, said penetrable liquid being adapted to form carbon upon thermal treatment;
   thermally treating the ceramic body after penetration to carbonize the penetrable liquid thereby forming an electrically conductive layer in any such void present in the ceramic body; and
   detecting the presence or absence of the void by measuring electrical conductivity between two points separated from each other and shorted by said electrically conductive layer.

2. The process of claim 1, wherein the measured electrical conductivity is compared with a known electrical conductivity to determine the presence or absence of the voids.

3. The process of claim 1, wherein said penetrable liquid comprises a hydrocarbon.

4. The process of claim 1, wherein said ceramic bodies are made of a material selected from the group consisting of electric materials, electronic materials, magnetic materials, structural materials and cutting materials including zirconia, alumina, magnesia, mullite, ZnO, barium titanate, glass, $\beta$-almunia, silicon nitride, silicon carbide and boron nitride.

5. The process of claim 1, wherein said two points are present on opposite surfaces of a partition wall of said ceramic body.

6. The process of claim 1, wherein at least one of said two points is an electrode preliminarily provided inside said ceramic body.

7. The process of claim 1, wherein said two points are electrodes provided on opposite surfaces of a partition wall of said ceramic body.

8. The process of claim 1, wherein said two points are electrodes provided on a surface of said ceramic body.

9. The process of claim 1 wherein said thermal treatment comprises a step of heating the ceramic body at a heating temperature within a range of 300°–600° C.

10. The process of claim 9, wherein said detecting step is carried out at a temperature 100° C. to 200° C. lower than said heating temperature.

11. A process for detecting voids in an oxygen sensor, comprising:
    penetrating a penetrable liquid into any void present in the oxygen sensor, said penetrable liquid being adapted to form carbon upon thermal treatment;
    thermally treating the oxygen sensor after penetration to carbonize the penetrable liquid thereby forming an electrically conductive layer in any such void present in the oxygen sensor; and
    detecting the presence or absence of the void by measuring electrical conductivity between two points separated from each other and shorted by said electrically conductive layer.

* * * * *